US00PP22265P2

(12) United States Plant Patent
Misato

(10) Patent No.: US PP22,265 P2
(45) Date of Patent: Nov. 22, 2011

(54) ***VERBENA* PLANT NAMED 'SUNTAPICORE'**

(50) Latin Name: *Verbena×hybrida*
Varietal Denomination: Suntapicore

(75) Inventor: Tomoya Misato, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 8 days.

(21) Appl. No.: 12/799,847

(22) Filed: May 4, 2010

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt
(74) *Attorney, Agent, or Firm* — C. A. Whealy

(57) ABSTRACT

A new and distinct cultivar of *Verbena* plant named 'Suntapicore', characterized by its compact, upright to trailing plant habit; vigorous growth habit; freely branching habit; early and freely flowering habit; and vivid red-colored flowers that are held above and beyond the foliar plane.

1 Drawing Sheet

Botanical designation: *Verbena×hybrida.*
Cultivar denomination: 'SUNTAPICORE'.

BACKGROUND OF THE INVENTION

The present invention relates to a new and distinct cultivar of *Verbena* plant, botanically known as *Verbena×hybrida*, and hereinafter referred to by the name 'Suntapicore'.

The new *Verbena* plant is a product of a planned breeding program conducted by the Inventor in Higashiomi, Shiga, Japan. The objective of the breeding program is to create new compact and trailing *Verbena* plants with freely branching habit and attractive flower coloration.

The new *Verbena* plant originated from a cross-pollination made by the Inventor in November, 2004 in Higashiomi, Shiga, Japan of a proprietary selection of *Verbena×hybrida* identified as code number T69-00-1, not patented, as the female, or seed, parent with a proprietary selection of *Verbena×hybrida* identified as code number VW411, not patented, as the male, or pollen, parent. The new *Verbena* plant was discovered and selected by the Inventor as a single flowering plant within the progeny of the stated cross-pollination in a controlled environment in Higashiomi, Shiga, Japan in October, 2005.

Asexual reproduction of the new *Verbena* plant by cuttings in a controlled environment in Higashiomi, Shiga, Japan since November, 2005 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environment and cultural practices such as temperature and light intensity without, however, any variance in genotype.

The following traits have been repeatedly observed and are determined to be the unique characteristics of 'Suntapicore'. These characteristics in combination distinguish 'Suntapicore' as a new and distinct cultivar of *Verbena* plant:

1. Compact, upright to trailing plant habit.
2. Vigorous growth habit.

3. Freely branching habit.
4. Early and freely flowering habit.
5. Vivid red-colored flowers that are held above and beyond the foliar plane.

Plants of the new *Verbena* can be compared to plants of the female parent selection. Plants of the new *Verbena* differ from plants of the female parent selection in the following characteristics:

1. Plants of the new *Verbena* are taller than plants of the female parent selection.
2. Leaf margins of plants of the new *Verbena* are pinnately cleft whereas leaf margins of plants of the female parent selection are shallowly lobed.

Plants of the new *Verbena* can be compared to plants of the male parent selection. Plants of the new *Verbena* differ from plants of the male parent selection in the following characteristics:

1. Leaf margins of plants of the new *Verbena* are pinnately cleft whereas leaf margins of plants of the male parent selection are pinnately parted.
2. Plants of the new *Verbena* and the male parent selection differ in flower color as plants of the male parent selection have darker red-colored flowers.

Plants of the new *Verbena* can be compared to plants of the *Verbena×hybrida* 'Oxena', disclosed in U.S. Plant Pat. No. 13,126. In side-by-side comparisons conducted in Higashiomi, Shiga, Japan, plants of the new *Verbena* differed from plants of 'Ozena' in the following characteristics:

1. Plants of the new *Verbena* were more trailing than and not as upright and spreading as plants of 'Oxena'.
2. Plants of the new *Verbena* were more compact than plants of 'Ozena'.
3. Plants of the new *Verbena* have larger inflorescences than plants of 'Oxena'.

BRIEF DESCRIPTION OF THE PHOTOGRAPHS

The accompanying colored photographs illustrate the overall appearance of the new *Verbena* plant, showing the colors as true as it is reasonably possible to obtain in colored reproductions of this type. Colors in the photographs may differ slightly from the color values cited in the detailed botanical description which accurately describe the colors of the new *Verbena* plant.

The photograph at the top of the sheet comprises a side perspective view of a typical flowering plant of 'Suntapicore' grown in a container.

The photograph at the bottom of the sheet is a close-up view of a typical flowering plant of 'Suntapicore'.

DETAILED BOTANICAL DESCRIPTION

The aforementioned photographs and following observations and measurements describe plants grown during the early summer in 15-cm containers in an outdoor nursery in Higashiomi, Shiga, Japan, under commercial practice with day temperatures averaging 23° C. and night temperatures averaging 13° C. Plants were four months old when the photographs and description were taken. In the following description, color references are made to The Royal Horticultural Society Colour Chart, 2001 Edition, except where general terms of ordinary dictionary significance are used.

Botanical classification: *Verbena×hybrida* 'Suntapicore'.

Parentage:

*Female, or seed, parent.*—Proprietary selection of *Verbena×hybrida* identified as code number T69-00-1, not patented.

*Male, or pollen, parent.*—Proprietary selection of *Verbena×hybrida* identified as code number VW411, not patented.

Propagation:

*Type.*—By cuttings.

*Time to initiate roots.*—About 10 to 14 days at 20° C. to 25° C.

*Time to produce a rooted young plant.*—About four weeks at 20° C. to 25° C.

*Root description.*—Fibrous; white in color.

*Rooting habit.*—Freely branching.

Plant description:

*Plant and growth habit.*—Initially upright, then outwardly spreading to trailing growth habit; lateral branches decumbent; freely branching habit, pinching enhances lateral branch development; vigorous growth habit.

*Plant height.*—About 12.6 cm.

*Plant diameter.*—About 31.4 cm.

Lateral branch description:

*Length.*—About 14.6 cm.

*Diameter.*—About 1.3 mm.

*Internode length.*—About 1.4 cm.

*Strength.*—Strong.

*Texture.*—Pubescent.

*Color.*—Close to 144A.

Foliage description:

*Arrangement.*—Opposite, simple.

*Length.*—About 3.8 cm.

*Width.*—About 2.2 cm.

*Shape.*—Ovate.

*Apex.*—Acute.

*Base.*—Cuneate.

*Margin.*—Pinnately cleft.

*Texture, upper and lower surfaces.*—Coarse; pubescent.

*Venation pattern.*—Pinnate; reticulate.

*Color.*—Developing and fully expanded leaves, upper surface: Close to 137B; venation, close to 145B. Developing and fully expanded leaves, lower surface: Close to 137C; venation, close to 145B.

*Petiole.*—Length: About 3.3 mm. Diameter: About 1.6 mm. Texture, upper and lower surfaces: Sparsely pubescent. Color, upper and lower surfaces: Close to 145B.

Flower description:

*Flower arrangement and habit.*—Salverform flowers arranged in hemispherical terminal racemes; flowers face mostly upright; flowers sessile; freely flowering habit with about 16 flowers per inflorescence and about 14 inflorescences per plant.

*Natural flowering season.*—Plants flower continuously from spring to late autumn in Japan; plants begin flowering about four weeks after planting.

*Flower longevity.*—Flowers last about one week on the plant; flowers not persistent.

*Fragrance.*—None detected.

*Inflorescence diameter.*—About 4.2 cm.

*Flowers.*—Appearance: Flared trumpet, corolla fused, five-parted. Diameter: About 1.5 cm. Depth (height): About 1.7 cm. Tube length: About 1.5 cm. Tube diameter: About 1 mm.

*Flower buds.*—Length: About 2 cm. Diameter: About 1.2 mm. Shape: Clavate. Color: Close to 46A.

*Corolla.*—Arrangement: Single whorl of five fused petals. Petal length: About 6 mm. Petal width: About 5 mm. Petal lobe shape: Cordate. Petal lobe apex: Cordate. Petal lobe margin: Entire. Petal texture, upper and lower surfaces: Smooth, glabrous. Color: Petal, when opening, upper surface: Close to 45A; around the throat, close to 46A. Petal, when opening, lower surface: Close to 47B. Petal, fully opened, upper surface: Close to 45A; around the throat, close to 46A; color becoming closer to 46B with development. Petal, fully opened, lower surface: Close to 47D; towards the margins, close to 47A. Throat: Close to 186B. Tube: Close to 186B.

*Calyx.*—Arrangement: One single narrow calyx tube per flower with five fused sepals. Sepal length: About 1.5 mm. Sepal width: About 0.9 mm. Sepal shape: Lanceolate. Sepal apex: Acute. Sepal margin: Entire. Sepal texture, upper and lower surfaces: Pubescent. Sepal color, upper and lower surfaces: Close to 138A.

*Peduncles.*—Length: About 3.1 cm. Diameter: About 1.1 mm. Strength: Strong. Texture: Pubescent. Color: Close to 144A.

*Reproductive organs.*—Stamens: Quantity/arrangement: Four per flower, adnate to corolla tube. Anther shape: Ellipsoidal. Anther size: About 0.9 mm by 0.5 mm. Anther color: Close to 149C. Pollen amount: Scarce. Pistils: Quantity: One per flower. Pistil length: About 1.4 cm. Stigma shape: Bi-parted. Stigma color: Close to 138B. Style color: Close to 145D. Ovary color: Close to 144B. Fruits/seed: Fruit and seed development have not been observed.

Temperature tolerance: Plants of the new *Verbena* have been observed to tolerate temperatures from about 0° C. to about 35° C.

Pathogen/pest resistance: Plants of the new *Verbena* have not been observed to be resistant to pathogens and pests common to *Verbena* plants.

It is claimed:

1. A new and distinct *Verbena* plant named 'Suntapicore' as illustrated and described.

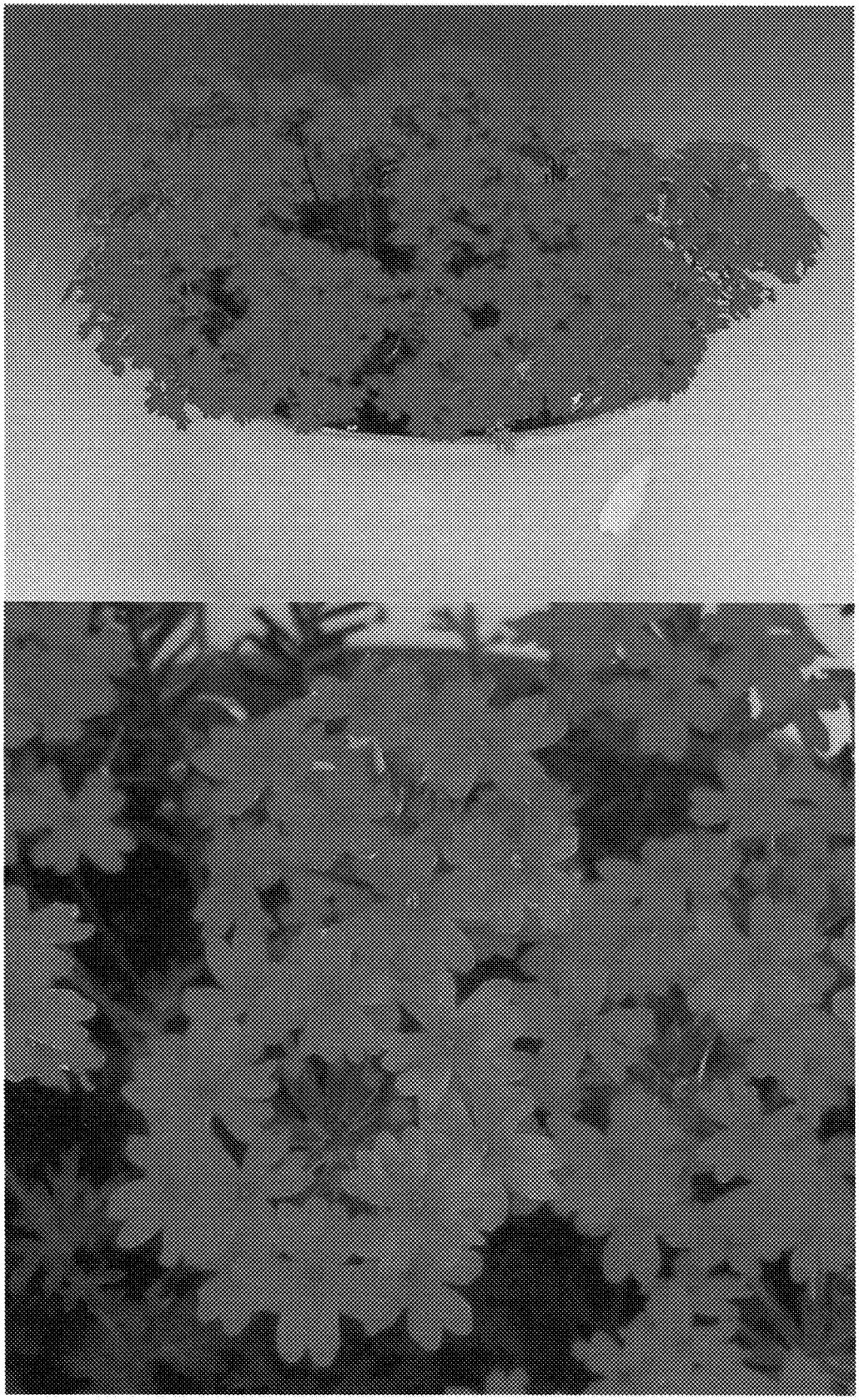

* * * * *